US010520417B2

(12) United States Patent
Ono et al.

(10) Patent No.: US 10,520,417 B2
(45) Date of Patent: Dec. 31, 2019

(54) ANALYSIS METHOD AND ANALYSIS DEVICE

(71) Applicant: JVC KENWOOD Corporation, Yokohama-shi, Kanagawa (JP)

(72) Inventors: Masayuki Ono, Yokohama (JP); Makoto Itonaga, Yokohama (JP); Yuichi Hasegawa, Yokohama (JP); Koji Tsujita, Yokohama (JP); Shigehiko Iwama, Yokohama (JP)

(73) Assignee: JVC KENWOOD CORPORATION, Yokohama-Shi, Kanagawa (JP)

( * ) Notice: Subject to any disclaimer, the term of this patent is extended or adjusted under 35 U.S.C. 154(b) by 0 days.

(21) Appl. No.: 16/176,264

(22) Filed: Oct. 31, 2018

(65) Prior Publication Data

US 2019/0064048 A1 Feb. 28, 2019

Related U.S. Application Data

(63) Continuation of application No. PCT/JP2017/016894, filed on Apr. 28, 2017.

(30) Foreign Application Priority Data

May 16, 2016 (JP) ................................. 2016-097830

(51) Int. Cl.
*G01N 15/10* (2006.01)
*G01N 35/00* (2006.01)
(Continued)

(52) U.S. Cl.
CPC ........... *G01N 15/10* (2013.01); *G01N 33/553* (2013.01); *G01N 33/587* (2013.01);
(Continued)

(58) Field of Classification Search
CPC ........... G01N 33/54373; G01N 33/587; G01N 35/00069; G01N 15/10; G01N 2015/1062; B01L 2300/0806
See application file for complete search history.

(56) References Cited

U.S. PATENT DOCUMENTS

| 5,922,537 | A | 7/1999 | Ewart et al. |
| 6,025,202 | A | 2/2000 | Natan |

(Continued)

FOREIGN PATENT DOCUMENTS

| JP | 2002530786 A | 9/2002 |
| JP | 2009115665 A | 5/2009 |

(Continued)

OTHER PUBLICATIONS

Mayer, Kathryn M., et al., "A single molecule immunoassay by localized surface plasmon resonance", Nanotechnology 21 (2010) 255503 (8pp).

(Continued)

*Primary Examiner* — Maurice C Smith
(74) *Attorney, Agent, or Firm* — Nath, Goldberg & Meyer; Jerald L. Meyer; Stanley N. Protigal

(57) ABSTRACT

An analysis method irradiates, with laser light, an analysis substrate made of a resin material and having a reaction region on which detection target substances and nanoparticles of a metal compound for labeling the detection target substances are captured. The analysis method extracts, as a substrate signal level, a signal level generated when receiving reflected light from the analysis substrate. The analysis method receives reflected light from the reaction region to generate a light reception level signal. The analysis method extracts a nanoparticle detection signal from the light reception level signal of the reflected light from the reaction region, the nanoparticle detection signal having a higher level than the signal level of the reflected light from the (Continued)

analysis substrate. The analysis method detects the nanoparticles in accordance with the extracted nanoparticle detection signal.

4 Claims, 6 Drawing Sheets

(51) Int. Cl.
*G01N 33/553* (2006.01)
*G01N 33/58* (2006.01)
*G01N 35/04* (2006.01)
*G01N 15/00* (2006.01)

(52) U.S. Cl.
CPC .......... *G01N 35/00069* (2013.01); *B01L 2300/0806* (2013.01); *G01N 35/04* (2013.01); *G01N 2015/0038* (2013.01); *G01N 2015/1062* (2013.01); *G01N 2035/0437* (2013.01)

(56) References Cited

U.S. PATENT DOCUMENTS

| | | | | |
|---|---|---|---|---|
| 7,812,318 B1* | 10/2010 | Auld | ........... | G01N 35/00069 250/395 |
| 2002/0176342 A1* | 11/2002 | Worthington | ...... | G01N 15/1475 369/53.31 |
| 2003/0003457 A1* | 1/2003 | Golovlev | ............ | C12Q 1/6825 506/3 |
| 2005/0019901 A1* | 1/2005 | Matveeva | ............ | B01L 3/5025 506/9 |
| 2006/0171288 A1* | 8/2006 | Kuypers | ............ | G01N 33/5436 369/275.1 |
| 2014/0271366 A1* | 9/2014 | Denomme | ....... | G01N 33/54373 422/69 |

FOREIGN PATENT DOCUMENTS

JP    2013134083 A    7/2013
WO    2016052118 A1    4/2016

OTHER PUBLICATIONS

Teramura, Yuji, et al., "Surface plasmon resonance-based highly sensitive immunosensing for brain natriuretic peptide using nanobeads for signal amplicication", Analytical Chemistry 357 (2006), pp. 208-215.

European Search report dated Feb. 18, 2019, from counterpart application EP 17799161.9.

* cited by examiner

ANALYSIS METHOD AND ANALYSIS DEVICE

CROSS REFERENCE TO RELATED APPLICATION

This application is a Continuation of PCT Application No. PCT/JP2017/016894, filed on Apr. 28, 2017, and claims the priority of Japanese Patent Application No. 2016-097830, filed on May 16, 2016, the entire contents of both of which are incorporated herein by reference.

BACKGROUND

The present disclosure relates to an analysis method and an analysis device of analyzing biomaterials such as antigens and antibodies.

Immunoassays are known to quantitatively analyze disease detection and therapeutic effects by detecting particular antigens or antibodies as biomarkers associated with diseases.

Japanese Translation of PCT International Application Publication No. 2002-530786 (Patent Literature 1) discloses an analysis method and an analysis device in which antibodies that are fixed to a reaction region on an analysis substrate are allowed to bind to antigens that are detection target substances in a specimen, and the detection target substances further bound to nanoparticles are captured on the reaction region and scanned with laser light emitted from an optical pickup, so as to detect the nanoparticles captured on the reaction region.

The conventional analysis method as disclosed in Patent Literature 1 scans the reaction region by emitting the laser light from the optical pickup, and analyzes the reflected light from the reaction region to detect the nanoparticles, so as to detect the detection target substances indirectly. The analysis method and the analysis device disclosed in Patent Literature 1 are the application of an optical disc and an optical disc device to specimen detection.

SUMMARY

During the process of forming the reaction region, more particularly, in the steps of capturing the detection target substances on the analysis substrate by an antigen-antibody reaction, and washing out unreacted and unnecessary substances, an aggregation of proteins, salt contained in a cleaning liquid, or a surfactant may remain as residues in the reaction region. The residues are detected when the nanoparticles are detected.

Detection signals (noise signals) derived from residues and detection signals (nanoparticle detection signals) derived from nanoparticles typically have similar pulse waveforms. The conventional analysis method and analysis device cannot distinguish between the noise signals and the nanoparticle detection signals with a high accuracy. When the amount of detection target substances contained is quite small, nanoparticles binding to the detection target substances and captured on the reaction region are decreased to a quite small amount. As a result, influence of the noise signals is relatively increased, and accuracy of quantitatively analyzing the nanoparticles is decreased, which particularly leads to limitations on accurate detection of the nanoparticles, or a decrease in the accuracy of quantitation analysis of decomposition of the nanoparticles.

A first aspect of one or more embodiments provides an analysis method including: irradiating, with laser light, an analysis substrate made of a resin material and having a reaction region on which detection target substances and nanoparticles of a metal compound for labeling the detection target substances are captured; extracting, as a substrate signal level, a signal level generated when receiving reflected light from a non-reaction region in the analysis substrate at which the reaction region is not formed; receiving reflected light from the reaction region to generate a light reception level signal; extracting a nanoparticle detection signal having a higher signal level than the substrate signal level from the light reception level signal of the reflected light from the reaction region; and detecting the nanoparticles in accordance with the extracted nanoparticle detection signal.

A second aspect of one or more embodiments provides an analysis device including: an optical pickup configured to irradiate, with laser light, an analysis substrate made of a resin material and having a reaction region on which detection target substances and nanoparticles of a metal compound for labeling the detection target substance are captured, and to detect light reception levels of reflected light from the reaction region and a non-reaction region in the analysis substrate at which the reaction region is not formed so as to generate light reception level signals; a substrate level detection circuit configured to extract, as a substrate signal level, a signal level of a light reception level signal from the non-reaction region; a determination circuit configured to extract a nanoparticle detection signal having a higher signal level than the substrate signal level from the light reception level signal of the reflected light from the reaction region; and a counter circuit configured to detect the nanoparticles in accordance with the nanoparticle detection signal.

DETAILED DESCRIPTION

[Formation of Reaction Regions]

A method of forming reaction regions on an analysis substrate is described below with reference to FIG. 1 to FIG. 3.

Figure 1:
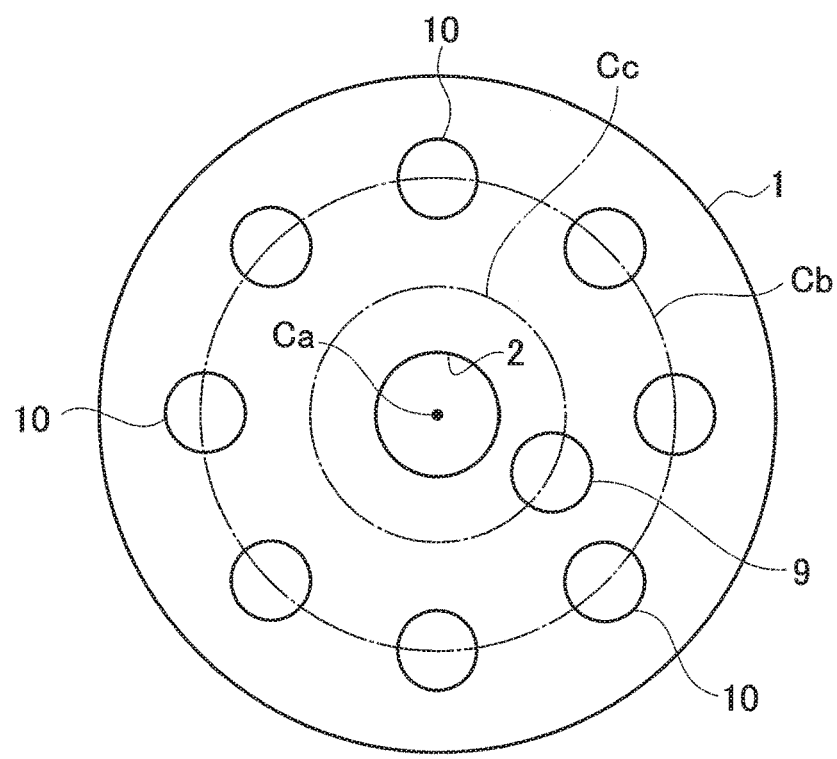
FIG. 1 is a top view of an analysis substrate provided with reaction regions.

As shown in FIG. 1, an analysis substrate 1 is formed into a circular shape having substantially the same dimensions as optical discs such as Blu-ray discs (BDs), DVDs, and compact discs (CDs). The analysis substrate 1 is provided with a positioning hole 2 in the middle.

The analysis substrate 1 is formed of resin material such as polycarbonate resin and cycloolefin polymer, commonly used for optical discs. The analysis substrate 1 is not limited to the optical discs described above, and may be any optical disc according to other embodiments or conforming to prescribed standards.

Figure 2:
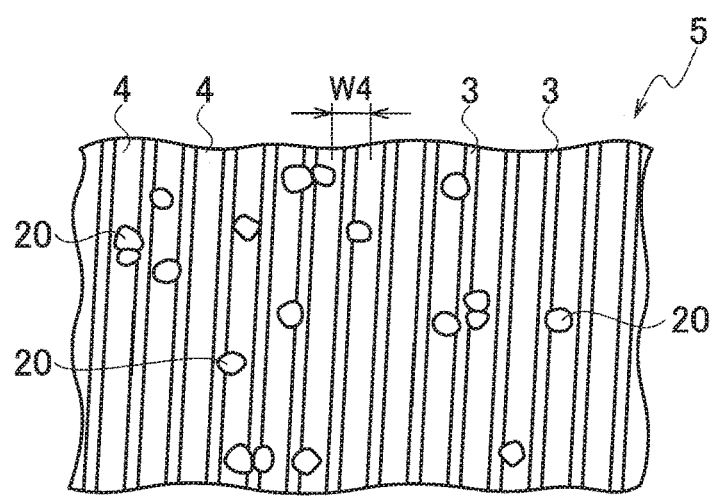
FIG. 2 is an enlarged schematic view illustrating a state in which nanoparticles are captured on a track region of a reaction region.
Figure 3:
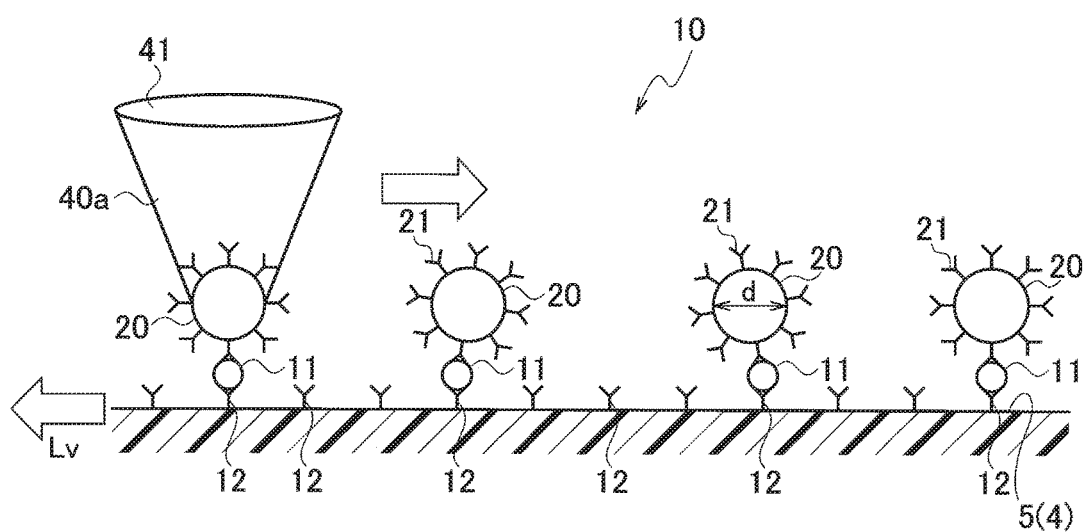
FIG. 3 is an enlarged schematic view illustrating a state in which nanoparticles specifically binding to detection target substances are captured on a track region of a reaction region.

As shown in FIG. 2, the surface of the analysis substrate 1 includes track regions 5 provided with convex regions 3 and recesses 4 alternately arranged in a radial direction. The convex regions 3 and the recesses 4 are formed in a spiral from the inner side to the outer side of the analysis substrate 1. A track pitch W4 of the recesses 4 (the convex regions 3) in the radial direction is 320 nanometers (nm), for example.

The track regions 5 of the analysis substrate 1 are provided with reaction regions 10. The method of forming the reaction regions 10 is described below with reference to FIG. 3.

Antibodies 12, which specifically bind to detection target substances 11 as particular antigens associated with a disease, are fixed to predetermined regions (in which the reaction regions 10 are formed) on the track regions 5. For example, a buffer solution including the antibodies 12 is reacted with the analysis substrate 1. The buffer solution after the reaction is then removed, and the analysis substrate 1 is washed and dried, so as to fix the antibodies 12 to the track regions 5. The detection target substances 11 are specific proteins, for example.

The detection target substances 11 are specifically bound to the antibodies 12 fixed to the track regions 5. For example, a sample solution, including the detection target substances 11, is reacted with the antibodies 12. The sample solution after the reaction is then removed, and the analysis substrate 1 is washed and dried, so as to capture the detection target substances 11 on the recesses 4 of the reaction regions 5. An outer diameter of the detection target substances 11 is 100 nm, for example. Sample solutions sometimes do not include the detection target substances 11. The following is a case in which the sample solution includes the detection target substances 11 for illustration purposes.

Nanoparticles 20 for labeling the detection target substances 11 specifically bind to the detection target substances 11 captured on the track regions 5. The surfaces of the nanoparticles 20 are provided with antibodies 21 specifically binding to the detection target substances 11. When the antibodies 21 of the nanoparticles 20 specifically bind to the detection target substances 11, the nanoparticles 20 are captured in the recesses 4 of the track regions 5. The size and material characteristics of the nanoparticles 20 are described below.

The detection target substances 11 and the nanoparticles 20 are thus captured in the recesses 4 of the track regions 5 of the analysis substrate 1. The regions in which the detection target substances 11 and the nanoparticles 20 are captured are the reaction regions 10 shown in FIG. 1. While FIG. 1 illustrates eight reaction regions 10 arranged at regular intervals such that the respective center points are located on the common circle Cb concentric with the analysis substrate 1 having the center Ca, the number and positions of the reaction regions 10 formed are not limited to this illustration.

[Analysis Device]

A configuration of an analysis device of detecting the nanoparticles 20 captured in the reaction regions 10 of the analysis substrate 1 is illustrated below with reference to FIG. 4.

The analysis device 1 includes a turntable 31, a clamper 32, a turntable drive unit 33, a turntable drive circuit 34, a guide shaft 35, an optical pickup 40, an optical pickup drive circuit 36, and a controller 37.

The analysis substrate 1 is placed on the turntable 31 with the reaction regions 10 facing down.

Figure 4:
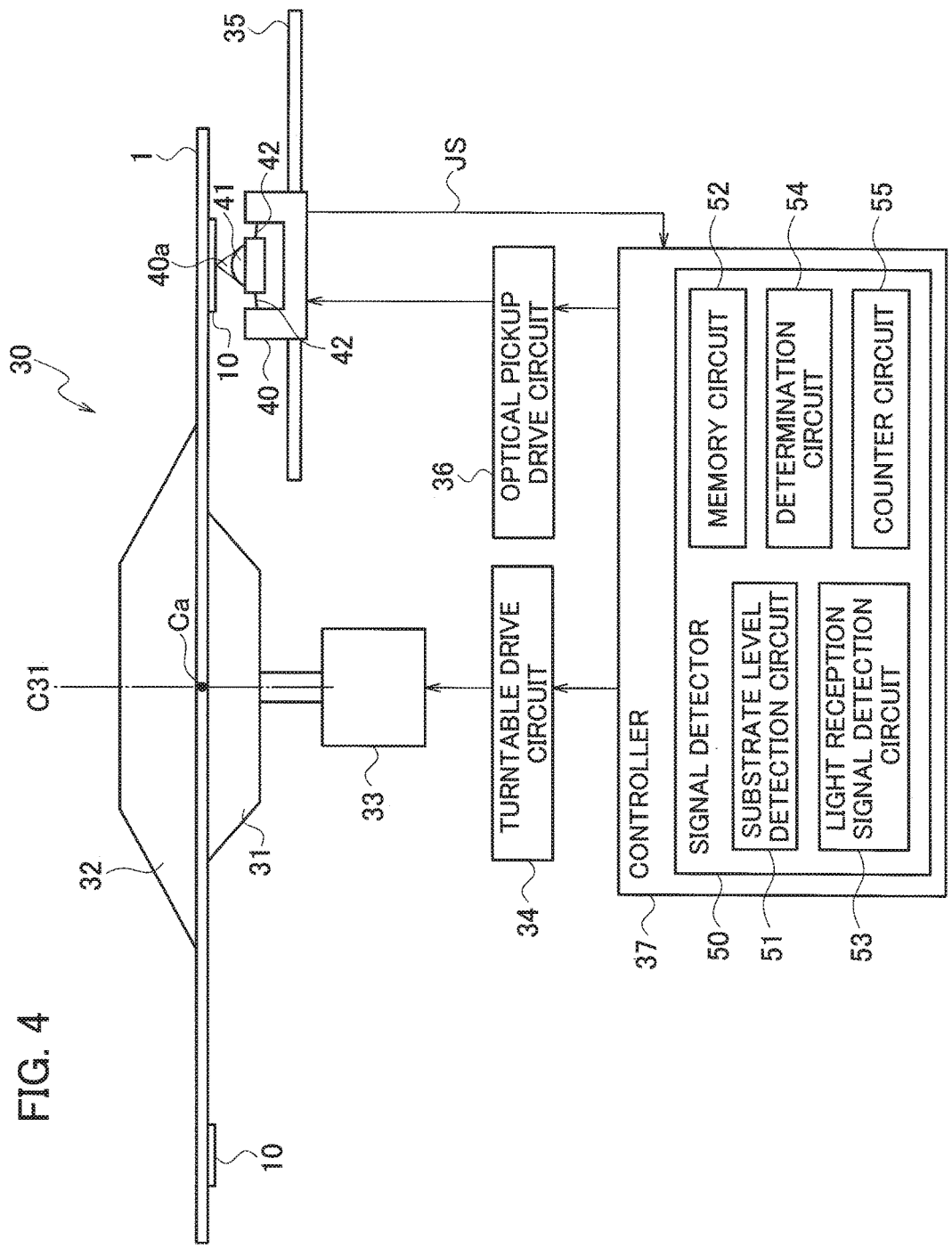
FIG. 4 is a configuration diagram showing an analysis device according to one or more embodiments.

The clamper 32 is driven in directions separating from and approaching the turntable 31, namely, in the upper and lower directions in FIG. 4. The analysis substrate 1 is held between the turntable 31 and the clamper 32 when the clamper 32 is driven downward. In particular, the analysis substrate 1 is held such that the center Ca is located on a rotation axis C31 of the turntable 31.

The turntable drive unit 33 drives the turntable 31 to rotate on the rotation axis C31 together with the analysis substrate 1 and the clamper 32. A spindle motor may be used as the turntable drive unit 33.

The turntable drive circuit 34 controls the turntable drive unit 33. For example, the turntable drive circuit 34 controls the turntable drive unit 33 such that the turntable 31 rotates at a constant linear velocity Lv together with the analysis substrate 1 and the clamper 32.

The guide shaft 35 is placed in parallel to the analysis substrate 1 in the radial direction of the analysis substrate 1. The guide shaft 35 is arranged in a direction perpendicular to the rotation axis C31 of the turntable 31.

The optical pickup 40 is supported by the guide shaft 35. The optical pickup 40 is driven along the guide shaft 35 in the radial direction of the analysis substrate 1 and in parallel to the analysis substrate 1. The optical pickup 40 is driven in a direction perpendicular to the rotation axis C31 of the turntable 31.

The optical pickup 40 includes an objective lens 41. The objective lens 41 is supported by suspension wires 42. The objective lens 41 is driven in the directions separating from and approaching the analysis substrate 1, namely, in the upper and lower directions in FIG. 4.

The optical pickup 40 emits laser light 40a to the analysis substrate 1. The laser light 40a is condensed by the objective lens 41 on the surface of the analysis substrate 1 provided with the reaction regions 10 (on the lower surface of the analysis substrate 1 in FIG. 4). The laser light 40a has a wavelength $\lambda$ of 405 nm, for example.

The optical pickup 40 receives the reflected light from the analysis substrate 1. The optical pickup 40 detects a light reception level of the reflected light, generates a light reception level signal JS, and outputs the signal to the controller 37.

The optical pickup drive circuit 36 controls the operation of the optical pickup 40. The optical pickup drive circuit 36 moves the optical pickup 40 along the guide shaft 35 or moves the objective lens 41 of the optical pickup 40 in the vertical direction, for example.

The controller 37 controls the turntable drive circuit 34 and the optical pickup drive circuit 36. A central processing unit (CPU) may be used as the controller 37, for example.

The controller 37 includes a signal detector 50 for detecting signals from the analysis substrate 1. The signal detector 50 includes a substrate level detection circuit 51, a memory circuit 52, a light reception signal detection circuit 53, a determination circuit 54, and a counter circuit 55.

The signal detector 50 extracts and counts the nanoparticle detection signals KS from the light reception level signal JS output from the optical pickup 40, so as to detect and quantitate the nanoparticles 20 captured in the reaction regions 10. It is difficult to directly detect the detection target substances 11, since the detection target substances 11 have a size as small as 100 nm. One or more embodiments detect and quantitate the nanoparticles 20 having a greater size than the detection target substances 11 so as to indirectly detect and quantitate the detection target substances 11 captured in the reaction regions 10.

[Nanoparticles and Detection of Nanoparticles]

Figure 5:
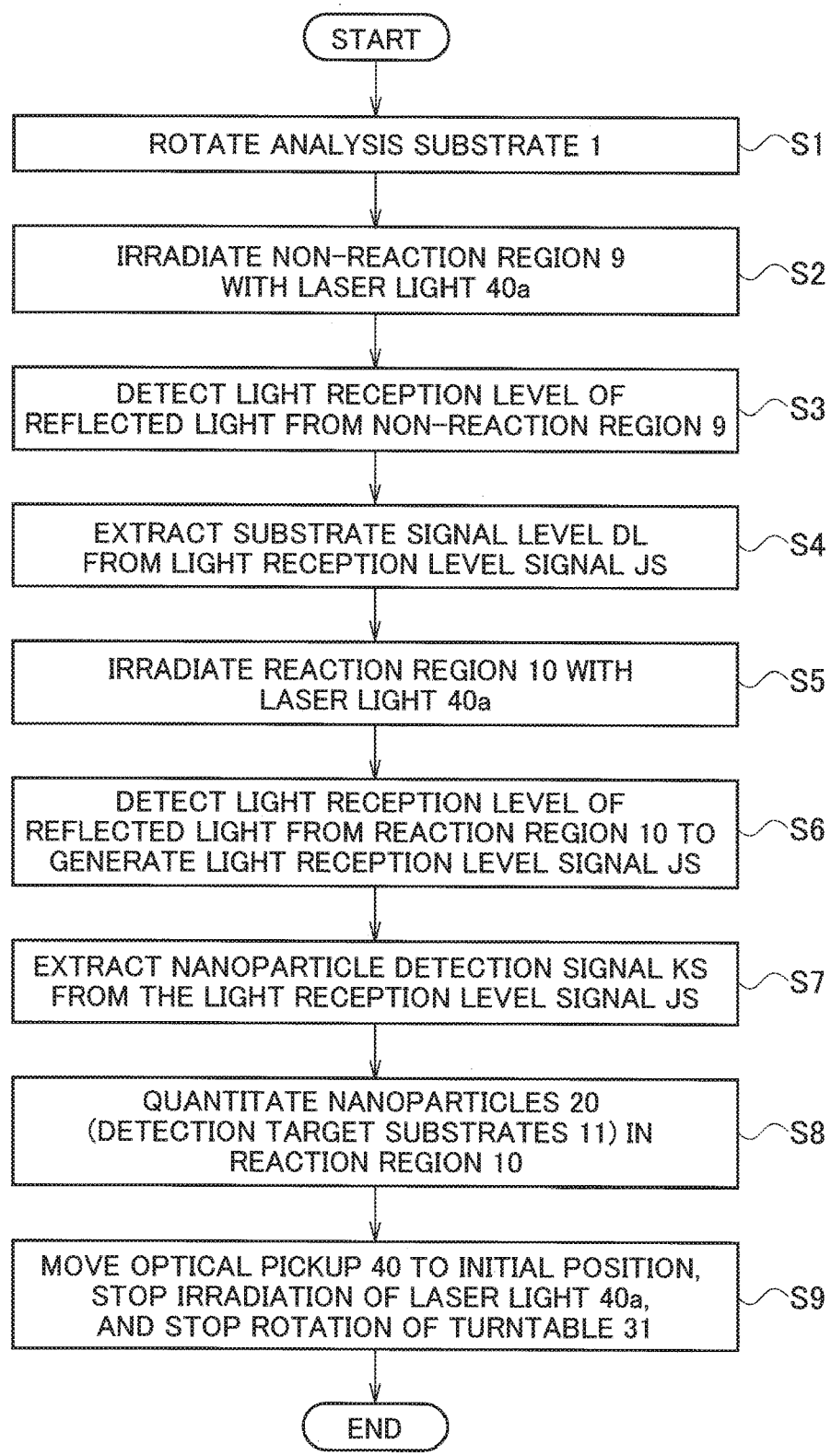
FIG. 5 is a flowchart for describing a method of analyzing nanoparticles according to one or more embodiments.

An analysis method of analyzing the nanoparticles 20 (the detection target substances 11) is described below with reference to the flowchart shown in FIG. 5. When a sample solution does not include the detection target substances 11, no detection target substance 11 or nanoparticle 20 is captured in the reaction regions 10 of the analysis substrate 1. The following is a case in which the detection target substances 11 and the nanoparticles 20 are captured in the reaction regions 10 for illustration purposes.

In step S1, the controller 37 controls the turntable drive circuit 34 to direct the turntable drive unit 33 to drive the turntable 31 so that the analysis substrate 1 provided with the reaction regions 10 rotates at a constant linear velocity Lv.

In step S2, the substrate level detection circuit 51 directs the optical pickup 40 to emit the laser light 40a to the analysis substrate 1, and controls the optical pickup drive circuit 36 to move the optical pickup 40 to a radial position of a predetermined non-reaction region 9 in the analysis substrate 1 at which the reaction region 10 is not formed. The non-reaction region 9 located on a circle Cc concentric with the analysis substrate 1 having the center Ca where the reaction region 10 is not provided as shown in FIG. 1, for example, is irradiated with the laser light 40a and scanned.

In step S3, the optical pickup 40 receives the reflected light from the non-reaction region 9. The optical pickup 40 detects a light reception level of the reflected light from the non-reaction region 9, generates a light reception level signal JS, and outputs the signal to the substrate level detection circuit 51.

In step S4, the substrate level detection circuit 51 extracts a light reception level of the light reception level signal JS of the non-reaction region 9 as a substrate signal level DL, and stores the extracted level in the memory circuit 52.

The substrate signal level DL depends on the substrate characteristics of the analysis substrate 1. The processing from step S2 to step S4 for extracting the substrate signal level DL does not need to be repeated every time the analysis substrate 1 is replaced when the analysis substrates 1 having the same design are used. The extraction of the substrate signal level DL may be performed only once during the operation of the analysis device 30, or may be repeated every time the lot of the analysis substrates 1 is changed to a new lot.

When the extraction of the substrate signal level DL is the first step, the processing from step S2 to step S4 may be omitted. One or more embodiments exemplify a case in which the light reception level signal JS from the non-reaction region 9 is obtained every time the analysis substrate 1 is replaced.

In step S5, the light reception signal detection circuit 53 directs the optical pickup 40 to emit the laser light 40a to the analysis substrate 1, and controls the optical pickup drive circuit 36 to move the optical pickup 40 to a radial position in the analysis substrate 1 at which the reaction region 10 is formed. As shown in FIG. 3, the reaction region 10 is irradiated with the laser light 40a and scanned along the recesses 4.

In step S6, the optical pickup 40 receives the reflected light from the reaction region 10. The optical pickup 40 detects the light reception level of the reflected light, generates a light reception level signal JS, and outputs the signal to the light reception signal detection circuit 53.

Figure 6:
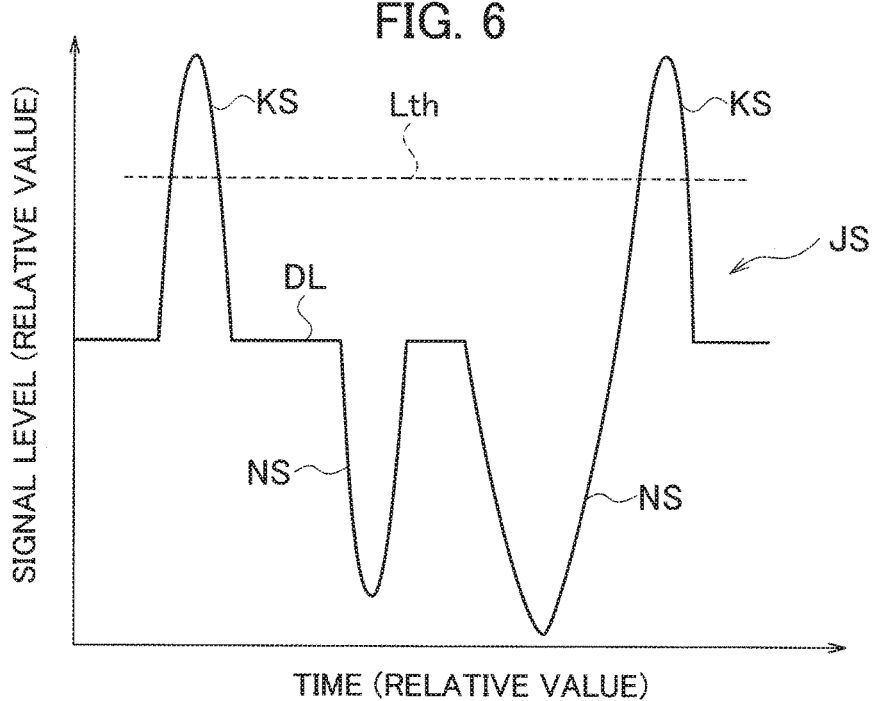
FIG. 6 is a graph illustrating a light reception level signal obtained by the analysis method according to one or more embodiments.

FIG. 6 is a graph showing an example of the light reception level signal JS obtained by the analysis method according to one or more embodiments. The vertical axis in FIG. 6 represents a signal level of the light reception level signal JS, and the horizontal axis represents a time. The light reception level of the reflected light from the reaction region 10, which is the reflected light from the analysis substrate 1, is referred to as a substrate signal level DL. The substrate signal level DL is in particular a light reception level of the reflected light from a recess 4 in the reaction region 10 of the analysis substrate 1.

A light reception level signal having a signal level (a high level) higher than the substrate signal level DL is a nanoparticle detection signal KS, and a light reception level signal having a signal level (a low level) lower than the substrate signal level DL is a noise signal NS. The substrate signal level DL in the light reception level signal JS is a constant light reception level during a period not including either the nanoparticle detection signal KS or the noise signal NS.

During the process of forming the reaction regions 10, more particularly, in the steps of capturing the detection target substances 11 on the analysis substrate 1 by an antigen-antibody reaction, and washing out unreacted and unnecessary substances, an aggregation of proteins, salt contained in a cleaning liquid, or a surfactant may remain as residues in the reaction regions 10. The noise signal NS derived from such residues is also detected as the light reception level signal JS.

Figure 7:
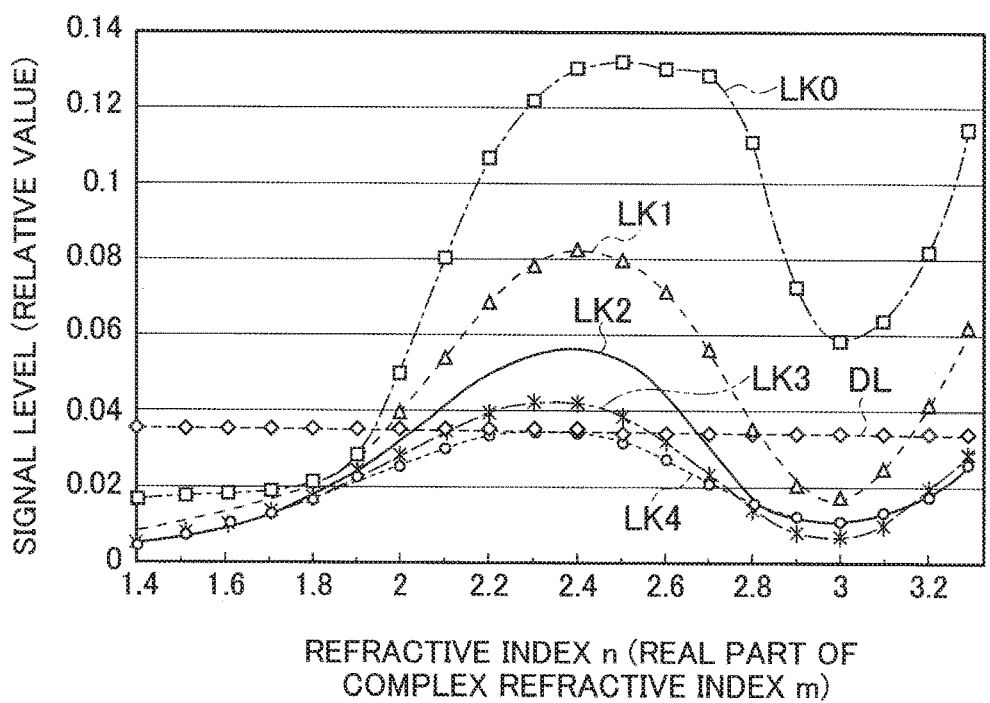
FIG. 7 is a graph showing a relationship between a complex refractive index of nanoparticles and a signal level of a light reception level signal obtained by a simulation.
Figure 8:
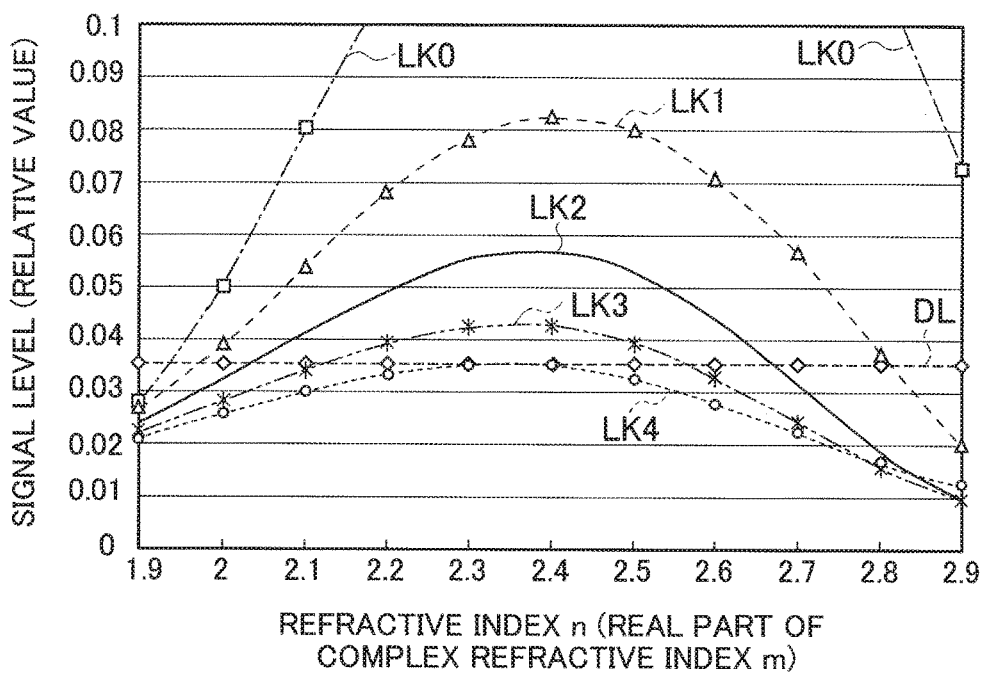
FIG. 8 is a partly-enlarged view of FIG. 7.

FIG. 7 is a graph showing a relationship between a complex refractive index m ($m=n-ki$) of nanoparticles and a signal level of a nanoparticle detection signal KS, obtained by an optical simulation by a finite-difference time-domain (FDTD) method. FIG. 8 is a partly-enlarged view of FIG. 7.

The vertical axis in each of FIG. 7 and FIG. 8 represents a signal level (a voltage relative value) of the nanoparticle detection signal KS, and the horizontal axis represents a refractive index n of a real part in the complex refractive index m of the nanoparticles. In the complex refractive index ($m=n-ki$), ki is an imaginary part, and k is an extinction coefficient. In FIG. 7 and FIG. 8, Lk0, Lk1, Lk2, Lk3, and Lk4 are signal levels of nanoparticle detection signals KS when $k=0$, $k=0.1$, $k=0.2$, $k=0.3$, and $k=0.4$, and DL is a substrate signal level. FIG. 7 and FIG. 8 each show a result of the optical simulation under the conditions that the laser light 40a has a wavelength λ of 405 nm, the outer diameter of the nanoparticles is 200 nm, and the refractive index n of the real part in the analysis substrate 1 is 1.53 ($ki=0$).

Figure 9:
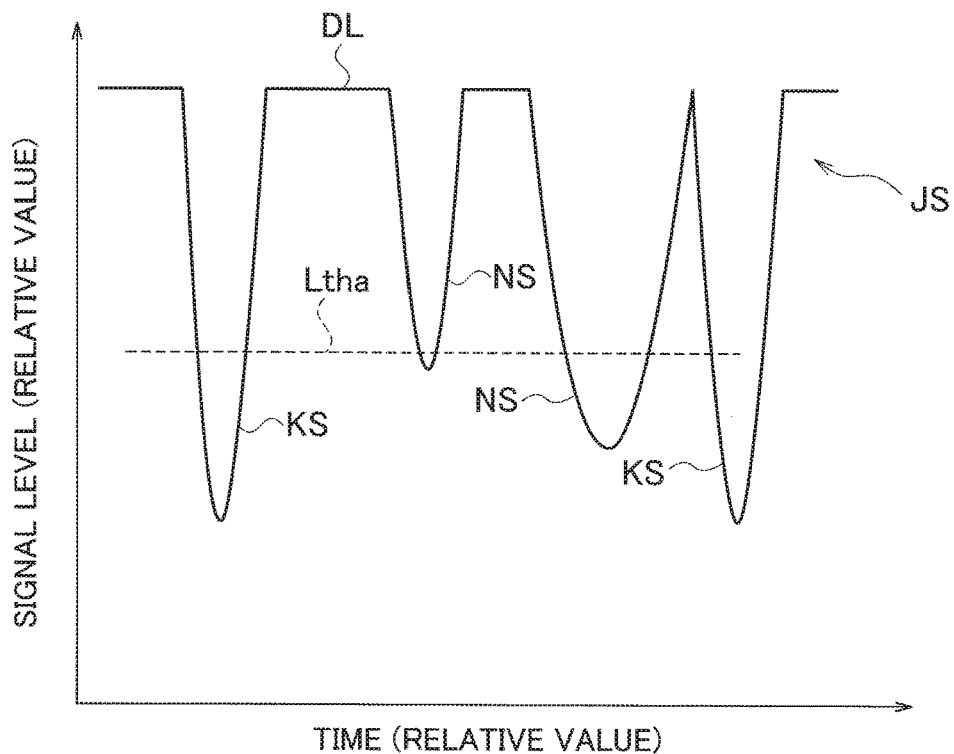
FIG. 9 is a graph illustrating a conventional light reception level signal.

FIG. 9 is a graph showing a relationship between conventional nanoparticle detection signals KS and noise signals NS. Conventionally, nanoparticles are made of synthetic resin such as polystyrene. Typical synthetic resin such as polystyrene has a refractive index n of about 1.5 and an extinction coefficient k of about 0.2 to 0.4. In the conventional case, the nanoparticle detection signals KS have signal levels lower than the substrate signal level DL, as shown in FIG. 9. The nanoparticle detection signals KS and the noise signals NS are thus detected as signal levels lower than the substrate signal level DL, as shown in FIG. 9.

Nanoparticle detection signals KS typically have lower signal levels than noise signals NS. It is thus possible to distinguish between the nanoparticle detection signals KS and the noise signals NS with some accuracy by comparing the respective signal levels of the light reception level signals with a threshold Ltha. However, if the amount of nanoparticles detected is quite small, an influence of the noise signals NS is relatively increased, decreasing the accuracy of quantitating nanoparticles.

One or more embodiments use the nanoparticles 20 of which the nanoparticle detection signals KS have higher signal levels than the substrate signal level DL. In particular, the nanoparticles 20 are made of material having a complex refractive index (m=n−ki), where an extinction coefficient k of an imaginary part is 0.3 or smaller (k≤0.3) and a refractive index n of a real part is in a range of 2.1 to 2.5 (2.1≤n≤2.5), or where an extinction coefficient k of an imaginary part is 0.2 or smaller (k≤0.2) and a refractive index n of a real part is in a range of 2.1 to 2.6 (2.1≤n≤2.6). Such material may be a metal compound including an oxide of transition metal such as titanium oxide, niobium oxide, and tantalum oxide.

The surfaces of the nanoparticles 20 may be polymerized and covered with resin material in order to provide a ligand. The effective complex refractive index of the nanoparticles 20 thus leads to a synthetic complex refractive index of the metal compound and the resin material. The polymerization covering of the surfaces of the nanoparticles 20 with such a thin resin film can provide a ligand. The nanoparticle detection signals KS can have higher signal levels than the substrate signal level DL when a refractive index n and an extinction coefficient k of the synthetic complex refractive index are set to the same ranges as described above.

A magnetic substance may be enclosed in the nanoparticles 20 in order to magnetically capture the nanoparticles 20. The effective complex refractive index of the nanoparticles 20 thus leads to a synthetic complex refractive index of the metal compound and the magnetic substance. The nanoparticle detection signals KS can have higher signal levels than the substrate signal level DL when a refractive index n and an extinction coefficient k of the synthetic complex refractive index are set to the same ranges as described above.

The reaction regions 10 are irradiated with the laser light 40a and scanned along the recesses 4. The nanoparticles 20 are preferably captured in the recesses 4 along the scanning direction with a high probability so as to quantitate the nanoparticles 20 accurately. If a diameter d of the nanoparticles 20 (refer to FIG. 3) is smaller than λ/4, the accuracy of detecting the nanoparticles 20 may be decreased, or some nanoparticles 20 may be captured and aligned in the direction orthogonal to the scanning direction to decrease the accuracy of quantitating the nanoparticles 20. The symbol "λ" represents a wavelength of the laser light 40a emitted to the nanoparticles 20.

If the diameter d of the nanoparticles 20 is greater than λ/2, the amount of the nanoparticles 20 captured in the recesses 4 is decreased. The diameter d of the nanoparticles 20 is therefore preferably in a range of λ/4 to λ/2 (λ/4≤d≤λ/2).

Returning to FIG. 5, in step S7, the determination circuit 54 determines that a light reception level signal with a signal level higher than the substrate signal level DL stored in the memory circuit 52 is the nanoparticle detection signal KS. For example, the determination circuit 54 compares the light reception level signal JS with a threshold Lth, and determines that the light reception level signal JS having the signal level greater than or equal to the threshold Lth is the nanoparticle detection signal KS. The threshold Lth is set to be a higher level than the substrate signal level DL.

The noise signals NS included in the light reception level signal JS can easily be distinguished from the nanoparticle detection signals KS, since the nanoparticle detection signals KS have higher signal levels than the substrate signal level DL and the noise signals NS have lower signal levels than the substrate signal level DL. Accordingly, only the nanoparticle detection signals KS can be extracted from the light reception level signal JS accurately.

In step S8, the counter circuit 55 counts the nanoparticle detection signals KS, in particular, the number of pulses of the nanoparticle detection signals KS for each reaction region 10, and sums up the counted values per track. The counter circuit 55 thus can quantitate the nanoparticles 20 in the reaction regions 10. The quantitation of the nanoparticles 20 leads to indirect quantitation of the detection target substances 11 labeled by the nanoparticles 20.

In step S9, the controller 37 controls the optical pickup drive circuit 36 to move the optical pickup 40 to the initial position, and stops the irradiation of the laser light 40a. The controller 37 then controls the turntable drive circuit 34 to stop the rotation of the turntable 31.

The analysis method according to one or more embodiments uses the nanoparticles 20 of which the nanoparticle detection signals KS have higher signal levels than the substrate signal level DL, so as to facilitate the distinction of the nanoparticle detection signals KS from noise signals having lower signal levels than the substrate signal level DL. For example, the light reception level signal JS is compared with the threshold Lth set to a higher level than the substrate signal level DL, so as to accurately extract only the nanoparticle detection signals KS from the light reception level signal JS. Accordingly, the nanoparticles 20 captured in the reaction regions 10 can be detected accurately in accordance with the nanoparticle detection signals KS extracted.

The analysis method according to one or more embodiments can extract nanoparticle detection signals with a higher accuracy than conventional methods to detect nanoparticles based on the extracted nanoparticle detection signals, so as to improve the accuracy of indirectly detecting detection target substances.

It should be understood that the present invention is not intended to be limited to one or more embodiments described above, and various modifications will be apparent to those skilled in the art without departing from the scope of the present invention.

What is claimed is:

1. An analysis method comprising:
   irradiating, with laser light, an analysis substrate made of a resin material and having a reaction region on which detection target substances and nanoparticles of a metal compound for labeling the detection target substances are captured;
   extracting, as a substrate signal level, a signal level generated when receiving reflected light from a non-reaction region in the analysis substrate at which the reaction region is not formed;
   receiving reflected light from the reaction region to generate a light reception level signal;
   extracting a nanoparticle detection signal having a higher signal level than the substrate signal level from the light reception level signal of the reflected light from the reaction region; and
   detecting the nanoparticles in accordance with the extracted nanoparticle detection signal,
   wherein the nanoparticles have a complex refractive index n−ki, where an extinction coefficient k of an imaginary part ki is 0.3 or smaller and a refractive index n of a real part is in a range of 2.1 to 2.5, or where an extinction coefficient k of an imaginary part ki is 0.2 or smaller and a refractive index n of a real part is in a range of 2.1 to 2.6.

2. The analysis method according to claim 1, wherein the nanoparticles are covered with a resin film.

3. The analysis method according to claim 1, wherein a magnetic body is enclosed in the nanoparticles.

4. An analysis device comprising:

an optical pickup configured to irradiate, with laser light, an analysis substrate made of a resin material and having a reaction region on which detection target substances and nanoparticles of a metal compound for labeling the detection target substance are captured, and to detect light reception levels of reflected light from the reaction region and a non-reaction region in the analysis substrate at which the reaction region is not formed so as to generate light reception level signals; and a controller comprising a substrate level detection circuit, a determination circuit, and a counter circuit, wherein the substrate level detection circuit is configured to extract, as a substrate signal level, a signal level of the light reception level signal from the non-reaction region acquired by the optical pickup, the determination circuit is configured to extract a nanoparticle detection signal having a higher signal level than the substrate signal level from the light reception level signal of the reflected light from the reaction region, and the counter circuit is configured to detect the nanoparticles in accordance with the nanoparticle detection signal.

* * * * *